(12) United States Patent
Gremel

(10) Patent No.: US 6,423,269 B1
(45) Date of Patent: Jul. 23, 2002

(54) PLEAT CONSTRUCTION FOR BELLOWS HEAT EXCHANGER MANIFOLD

(75) Inventor: Robert F. Gremel, Huntington Beach, CA (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 09/370,357

(22) Filed: Aug. 9, 1999

(51) Int. Cl.⁷ .................................................. A61M 1/14
(52) U.S. Cl. .......................................... 422/46; 165/164
(58) Field of Search .................... 422/44–46; 210/493.1, 210/321.6, 321.77, 321.78, 321.86, 321.87; 165/154, DIG. 357; 604/6.13, 6.14, 113; 261/158, 159, DIG. 28, DIG. 31

(56) References Cited

U.S. PATENT DOCUMENTS

| | | | | |
|---|---|---|---|---|
| 3,640,340 A | * | 2/1972 | Leonard et al. ............ | 165/166 |
| 4,585,056 A | * | 4/1986 | Oscarson .................... | 165/33 |
| 4,902,476 A | * | 2/1990 | Gordon et al. ............. | 422/46 |
| 5,058,661 A | * | 10/1991 | Oshiyama .................... | 165/70 |
| 5,120,501 A | * | 6/1992 | Mathewson et al. .......... | 422/46 |
| 5,421,405 A | * | 6/1995 | Goodin et al. ............... | 165/154 |
| 5,618,425 A | * | 4/1997 | Mitamura et al. ........ | 210/493.5 |
| 5,762,868 A | * | 6/1998 | Leonard ........................ | 422/46 |
| 5,762,869 A | * | 6/1998 | White et al. .................. | 422/48 |
| 5,951,949 A | * | 9/1999 | Olsen .......................... | 422/46 |
| 5,997,816 A | * | 12/1999 | McIntosh et al. ............. | 422/44 |
| 6,001,306 A | * | 12/1999 | McFall et al. ................ | 422/46 |

* cited by examiner

Primary Examiner—Angela D. Sykes
Assistant Examiner—Leslie R. Deak
(74) Attorney, Agent, or Firm—Stout, Uxa, Buyan & Mullins, LLP; Donald E. Stout

(57) ABSTRACT

Heat exchanging contact of water and blood with a pleated metal bellow heat exchanging surface in a heat exchanger for an extracorporeal blood circuit is improved by so forming the pleats of the bellows that the fluid chamber inside each pleat continuously narrows from the mouth of the pleat toward the inner end of the chamber. Uniform water distribution along the bellows is accomplished by making the water manifold in the heat exchanger core much larger in cross section than the inlet fitting to the manifold.

8 Claims, 3 Drawing Sheets

PLEAT CONSTRUCTION FOR BELLOWS HEAT EXCHANGER MANIFOLD

FIELD OF THE INVENTION

This invention relates to bellows heat exchangers for cardiovascular surgery equipment, and more particularly to efficiency improvements in such bellows heat exchangers.

BACKGROUND OF THE INVENTION

In cardiovascular surgery, a heart-lung machine provides an extracorporeal circuit in which the patient's blood is pumped and oxygenated while the heart is stopped. Because temperature control of the blood returned to the patient is important, a heat exchanger is typically provided in the circuit either as a separate unit or as part of the oxygenator. In a typical heat exchanger, water at a controlled temperature is conveyed along one side of a heat-conducting interface while blood is conveyed along the other side.

A problem of the prior art is that the conventional method of forming the bellows produces pleats in which fluid flowing into the pleat from either side must pass through a neck that is narrower than the fluid chamber formed by the pleat. This limits the efficiency of fluid penetration into the pleat, and therefore the heat transfer capacity of the bellows. In order to improve the exchange capacity of the bellows, it would be desirable to provide a manufacturing process which would eliminate this narrow neck.

Also, a problem occurs in conventional pleated heat exchangers due to the failure of the inner core of the heat exchanger to distribute water evenly over the full length of the bellows. One type of conventional core consists of a cylindrical body in which a water manifold having the same diameter as the inlet fitting is formed. This manifold is connected to the outside of the core through slots that extend longitudinally of the core. It has been found that this construction results in a kinetic energy distribution that causes an uneven flow out of the slots, particularly near the distal, closed end of the manifold.

SUMMARY OF THE INVENTION

The present invention enhances the heat exchange capacity of a pleated metal bellows type heat exchanger by providing an even, unobstructed fluid flow into the pleats of the bellows so as to maximize the amount of fluid which comes into contact with the heat exchange surface of the bellows. Specifically, the invention enhances fluid penetration into the pleats by so forming the pleats that the fluid path is widest at the mouth of the pleat and continuously narrows toward the inner end of the pleat's fluid chamber. In another aspect, the invention provides a water manifold structure that dissipates the kinetic energy of the water introduced into the heat exchanger and produces an even water flow into the pleats throughout the length of the bellows.

More particularly, there is provided a heat exchanger for controlling the temperature of blood in an extracorporeal circuit, which comprises a metal heat exchanging bellows having a first surface adapted for contact with blood and a second, separate surface adapted for contact with water. The metal bellows comprises a plurality of pleats defining at first set of fluid chambers on the first surface and a second set of fluid chambers on the second surface, wherein each fluid chamber in each of the first and second sets of fluid chambers has a mouth and an interior end, and is so shaped such that it is widest at the mouth and narrowest at the inner end. The inventive heat exchanger further comprises a water inlet and a manifold extending from the water inlet for directing water into a portion of the second set of fluid chambers through at least one slot.

In a further aspect of the invention, the fluid chambers in the first set of fluid chambers are substantially wider than the fluid chambers in the second set of fluid chambers. Preferably, the heat exchanger further comprises a housing, a blood inlet, and an annular space adapted to receive blood from the inlet, wherein the annular space is disposed between a radially outward side of the bellows and a wall of the housing. Portions of the first set of chambers are adapted to receive blood from the annular space.

In a preferred embodiment of the invention, the aforementioned pleats, in cross-section, have substantially the shape of a rectified sine wave, and each of the fluid chambers in each of the first and second sets of fluid chambers narrows continuously from its mouth toward its inner end. The heat exchanger further comprises a substantially cylindrical core, wherein the metal heat exchanging bellows surrounds the core and is substantially coaxial therewith. The water inlet comprises an inlet connector, and the manifold is disposed in the core. A cross-sectional area of the manifold is substantially larger than a cross-sectional area of the inlet connector, and includes a major lobe and a minor lobe interposed between the major lobe and the slot. The major lobe has a cross-sectional area substantially larger than the cross-sectional area of the inlet connector.

BRIEF DESCRIPTION OF THE DRAWINGS

FIG. 1b is a transverse vertical section along line 1b—1b of FIG. 1a;

FIG. 5b is a transverse vertical section along line 5b—5b of FIG. 5a.

DESCRIPTION OF THE PREFERRED EMBODIMENT

Figure 1A:
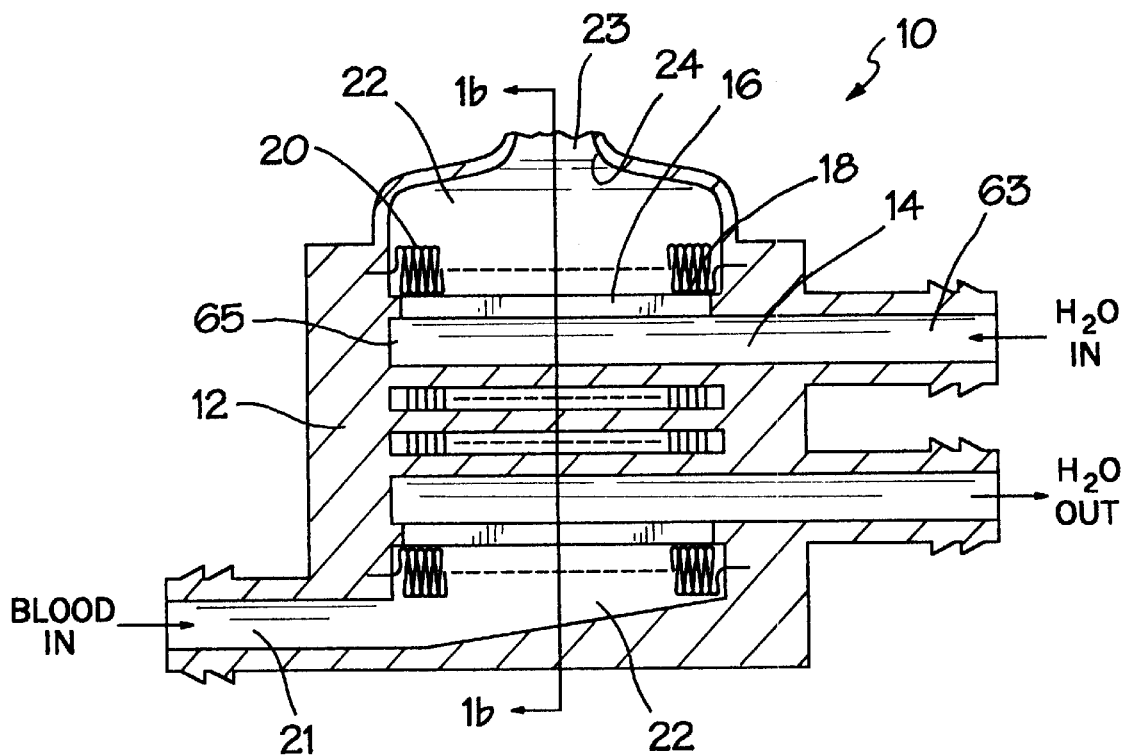
FIG. 1a is an axial vertical section of a typical prior art pleated metal heat exchanger.
Figure 1B:
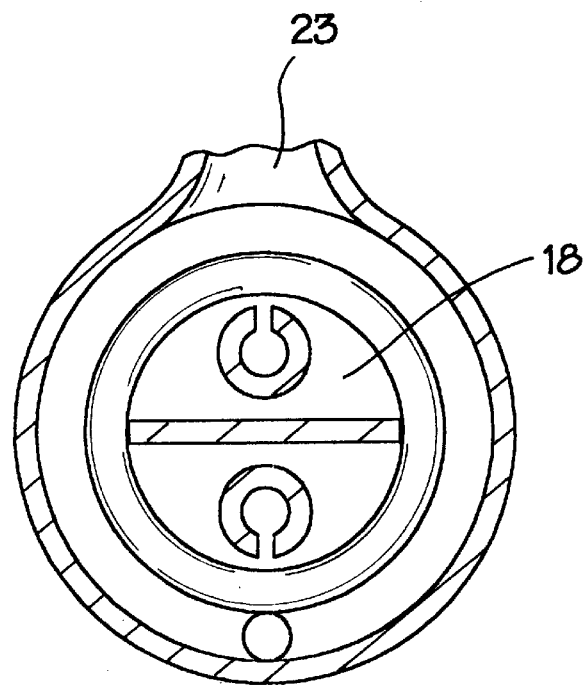

FIGS. 1a–b depict the conventional structure of a metal bellows heat exchanger 10. A core 12 contains a water manifold 14 which discharges water through a slot 16 into an annular space 18 radially inward of the metal bellows 20. Water is supplied to the manifold 14 through a fitting 63 which has the same cross-sectional area as the manifold. Blood is introduced from a connector 21 into the annular space 22 between the radially outward side of bellows 20 and the housing wall 24. Temperature-corrected blood flows out of heat exchanger 10 through the neck 23.

Figure 2:
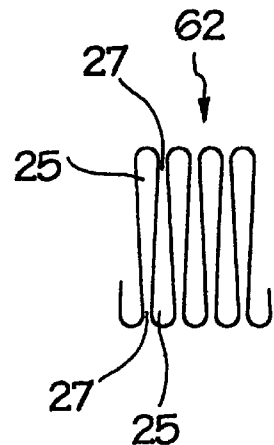
FIG. 2 is an enlarged section of a set of pleats in the prior art heat exchanger of FIGS. 1a and 1b.

FIG. 2 illustrates a typical conventional shape of the bellows 20. The formation of the pleats as illustrated in the center section of FIG. 4 results in pleats 62 that have inner fluid chambers 25 accessible only through a narrowed mouth 27.

Figure 3:
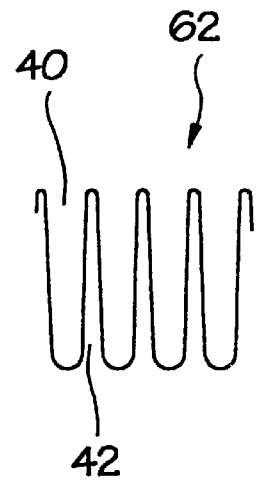
FIG. 3 is an enlarged section of a set of pleats in accordance with the invention.
Figure 4A:
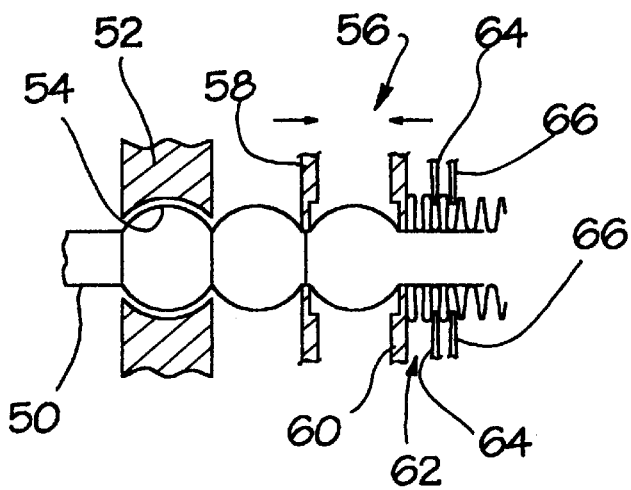
FIG. 4a is a schematic section of a metal tube showing the steps of its formation into a pleat.
Figure 4B:
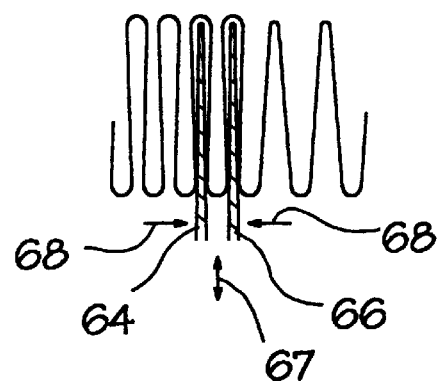
FIG. 4b is an enlarged detail section showing the third step in the formation of the pleat in accordance with the invention.

In one aspect of the invention (FIG. 3), depth penetration of fluid into the pleats 62 of the bellows 20 is improved by the process shown in FIG. 4b. This process forms the pleats 62 into a shape in which both the spaces 40 and the spaces 42 are widest at their mouths and become continuously narrower toward their inside ends. Thus, they do not exhibit the flow restriction that occurs at 27 in the prior art configuration of FIG. 2. In the construction of FIG. 3, it is preferable to have the wider spaces 40 on the blood side, and the narrower spaces 42 on the water side. This is so because the water flow is much faster (ca. 17–20 1/min) and inherently turbulent, while the blood flow is slower (ca. 5 1/min) and essentially laminar. Consequently, the water is better able to penetrate the pleats 62 than the blood is.

The configuration of FIG. 3 can be achieved during the manufacture of the bellows 20. Conventionally, the bellows 20 of FIG. 1 are formed from a metal tube 50. The tube 50 is first expanded and embossed in an embossing die set 52 (FIG. 4a). The expanded portion 54 is then placed in a pleating die 56 (FIG. 4a) whose faces 58, 60 are forced together so as to form the tube portion 54 into a pleat 62 which has a shape generally shown somewhat exaggeratedly in FIG. 2.

In accordance with the invention, a third fabrication step is used (FIGS. 4a and 4b) in which wedges 64, 66 are inserted into the pleats 62 (arrow 67) and brought together (arrows 68) so as to bend the pleats 62 into the shape of FIG. 3.

The conventional core construction shown in FIGS. 1a and 1b, in which the water inlet manifold 14 has essentially the same cross-sectional area as the inlet fitting 63, is subject to an uneven discharge pattern from the slot 16. Due to the kinetic energy of the water stream, the pressure of the water in the manifold 14 increases as the water approaches the closed end 65 of the manifold 14. Therefore, the water exits to slot 16 in a coherent flow near the water inlet fitting 63, but the flow from slot 16 becomes increasingly disrupted toward the distal, closed end 65 of the manifold 14. It eventually becomes a spray as it approaches the end 65 (FIG. 1a).

Figure 5A:
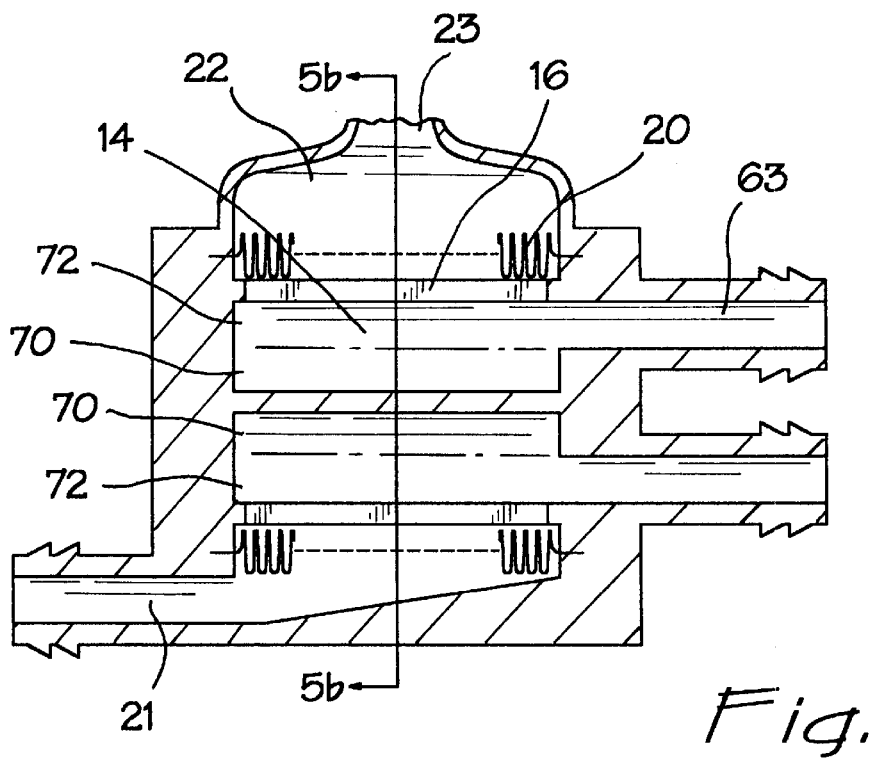
FIG. 5a is an axial vertical section of a heat exchanger using the water inlet manifold of this invention.
Figure 5B:
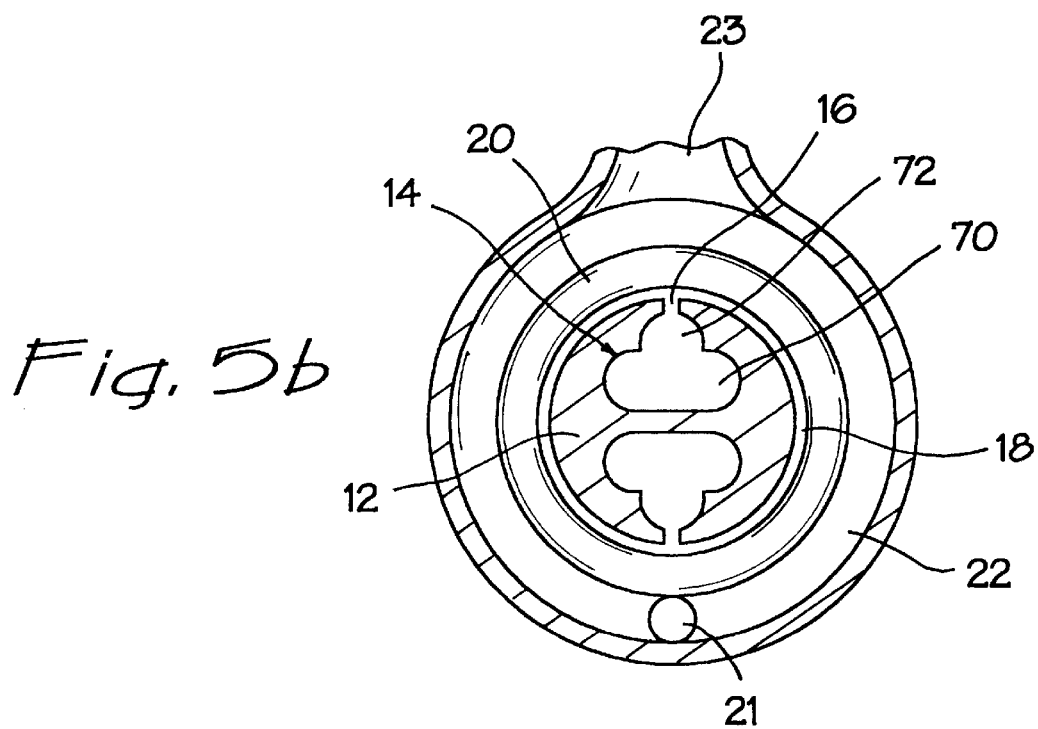

In accordance with the invention, a more even longitudinal distribution of the water flow emanating from the slots 16 is accomplished by making the cross-sectional area of inlet manifold 14 substantially larger than the cross-sectional area of the inlet water fitting 63 (FIGS. 5a and 5b). This dissipates the kinetic energy of the water in the manifold 14 and slows its flow sufficiently to provide an even outflow from the slot 16 throughout its length. Preferably, the manifold 14 is formed as shown in FIG. 5, with a major lobe 70 and a minor lobe 72 from which the slot 16 extends outwardly.

It is understood that the exemplary heat exchanger manifold and method of making the same described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

I claim:

1. A heat exchanger for controlling the temperature of blood in an extracorporeal circuit, comprising:

a metal heat exchanging bellows having a first surface adapted for contact with blood and a second, separate surface adapted for contact with water;

said metal bellows comprising a plurality of pleats defining a first set of fluid chambers on said first surface and a second set of fluid chambers on said second surface, wherein each fluid chamber in each of said first and second sets of fluid chambers has a mouth and an interior end, and is so shaped such that it is widest at said mouth and narrowest at said inner end;

a water inlet; and a manifold extending from said water inlet for directing water into a portion of said second set of fluid chambers through at least one slot.

2. The heat exchanger as recited in claim 1, wherein the fluid chambers in said first set of fluid chambers are substantially wider than the fluid chambers in said second set of fluid chambers.

3. The heat exchanger as recited in claim 1, and further comprising:

a housing;

a blood inlet; and an annular space adapted to receive blood from said inlet, said annular space being disposed between a radially outward side of said bellows and a wall of said housing.

4. The heat exchanger as recited in claim 3, wherein portions of said first set of chambers are adapted to receive blood from said annular space.

5. The heat exchanger as recited in claim 1, wherein said pleats, in cross-section, have substantially the shape of a rectified sine wave.

6. The heat exchanger as recited in claim 1, wherein each of said fluid chambers in each of said first and second sets of fluid chambers narrows continuously from said mouth toward said inner end.

7. The heat exchanger as recited in claim 1, and further comprising:

a substantially cylindrical core, said metal heat exchanging bellows surrounding said core and being substantially coaxial therewith;

said water inlet comprising an inlet connector; and said manifold being disposed in said core;

wherein a cross-sectional area of said manifold is substantially larger than a cross-sectional area of said inlet connector.

8. The heat exchanger as recited in claim 7, wherein said cross-sectional area of said manifold includes a major lobe and a minor lobe interposed between said major lobe and said slot, said major lobe having a cross-sectional area substantially larger than the cross-sectional area of said inlet connector.

* * * * *